United States Patent
Sachdev et al.

(10) Patent No.: US 11,308,614 B2
(45) Date of Patent: Apr. 19, 2022

(54) DEEP LEARNING FOR REAL-TIME COLON POLYP DETECTION

(71) Applicant: EndoVigilant Inc., Millersville, MD (US)

(72) Inventors: Vineet Sachdev, Millersville, MD (US); Ravindra Kompella, Hyderabad (IN); Hamed Pirsiavash, Ellicott City, MD (US)

(*) Notice: Subject to any disclaimer, the term of this patent is extended or adjusted under 35 U.S.C. 154(b) by 0 days.

(21) Appl. No.: 17/020,240

(22) Filed: Sep. 14, 2020

(65) Prior Publication Data

US 2021/0133964 A1    May 6, 2021

Related U.S. Application Data

(63) Continuation-in-part of application No. 16/359,822, filed on Mar. 20, 2019, now Pat. No. 10,841,514.

(60) Provisional application No. 62/949,520, filed on Dec. 18, 2019, provisional application No. 62/645,413, filed on Mar. 20, 2018.

(51) Int. Cl.
  *G06T 7/00* (2017.01)
  *G06T 5/00* (2006.01)
  *G06T 7/593* (2017.01)

(52) U.S. Cl.
  CPC ........... *G06T 7/0012* (2013.01); *G06T 5/005* (2013.01); *G06T 5/006* (2013.01); *G06T 5/008* (2013.01); *G06T 7/593* (2017.01); *G06T 2200/08* (2013.01); *G06T 2207/10016* (2013.01); *G06T 2207/10024* (2013.01); *G06T 2207/20036* (2013.01); *G06T 2207/20152* (2013.01); *G06T 2207/30028* (2013.01)

(58) Field of Classification Search
  None
  See application file for complete search history.

(56) References Cited

U.S. PATENT DOCUMENTS

| | | | |
|---|---|---|---|
| 9,530,205 B2 * | 12/2016 | Kim | G06K 9/346 |
| 9,741,116 B2 | 8/2017 | Liang et al. | |
| 9,747,687 B2 | 8/2017 | Tajbakhsh et al. | |
| 9,978,142 B2 | 5/2018 | Chi et al. | |
| 10,052,027 B2 | 8/2018 | Tajbakhsh et al. | |
| 10,055,843 B2 | 8/2018 | Tajbakhsh et al. | |
| 10,140,421 B1 * | 11/2018 | Bernard | A61B 8/565 |
| 11,132,794 B2 * | 9/2021 | Zur | G06T 7/246 |
| 2011/0301447 A1 * | 12/2011 | Park | G06T 7/0016 600/407 |

(Continued)

FOREIGN PATENT DOCUMENTS

WO    WO 2018/007139    1/2018

OTHER PUBLICATIONS

File History of U.S. Appl. No. 16/359,822, filed Mar. 20, 2019.
"YOLOv3: An Incremental Improvement" by Joseph Redmon and Ali Farhadi, University of Washington, Apr. 2018.

*Primary Examiner* — Edemio Navas, Jr.
(74) *Attorney, Agent, or Firm* — William H. Bollman

(57) ABSTRACT

A set of enhancements to further improve the performance of deep learning artificial intelligence algorithms trained to detect and localize colon polyps. The enhancements spanning training data mining efficiencies and automation, training data augmentation, early detection of polyps enable a more performant colon polyp detection solution for use on colonoscopy procedure recordings or live procedures in endoscopy centers.

11 Claims, 17 Drawing Sheets

(56) References Cited

U.S. PATENT DOCUMENTS

2014/0375768 A1  12/2014  Tsuchiya

* cited by examiner

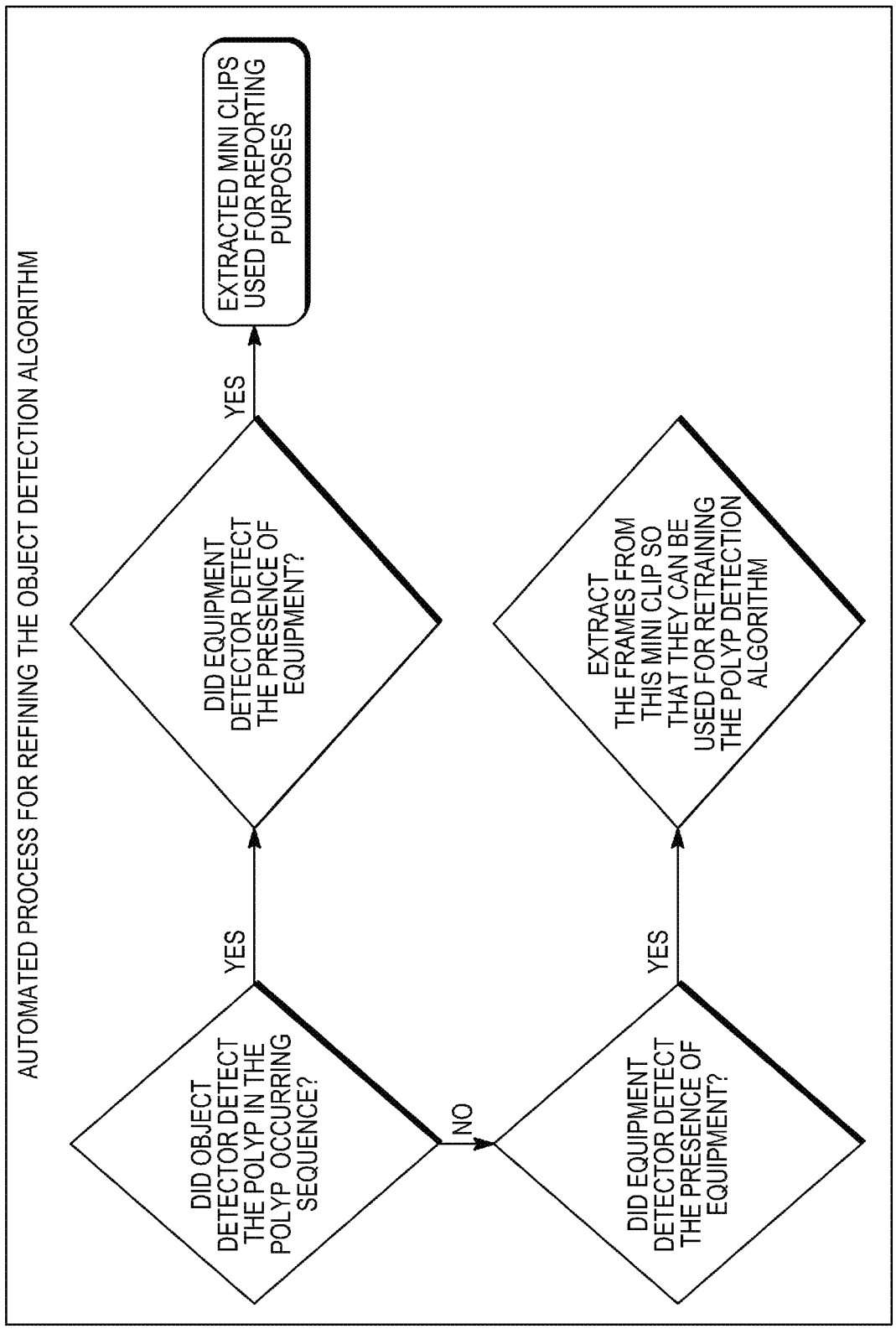

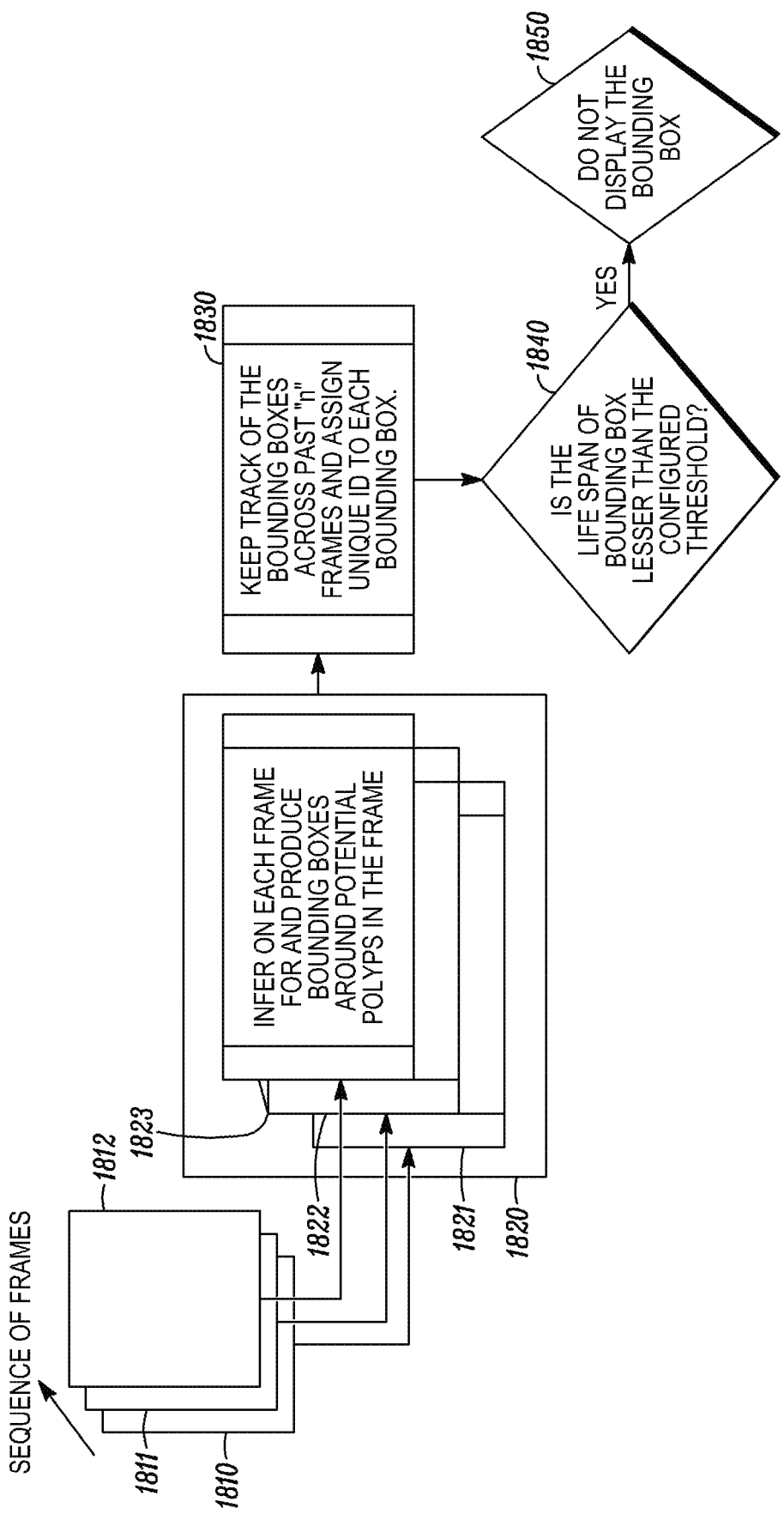

DEEP LEARNING FOR REAL-TIME COLON POLYP DETECTION

This application claims priority from U.S. Provisional No. 62/949,520 to "Methods for Improving Performance of Deep Learning Artificial Intelligence Algorithms for Real-Time Colon Polyp Detection" filed Dec. 18, 2019, the entirety of which is expressly incorporated herein by reference. The application also claims priority from U.S. patent application Ser. No. 16/359,822 to "Endoscopy Video Feature Enhancement Platform" filed Mar. 20, 2019, which in turn claims priority from U.S. Provisional No. 62/645,413 to "Endoscopy Video Feature Enhancement Platform Having Embedded Artificial Intelligence" filed Mar. 20, 2018, the entirety of all of which are also expressly incorporated herein by reference.

BACKGROUND OF THE INVENTION

1. Field of the Invention

The invention relates generally to real-time polyp detection in a colonoscopy video using deep learning artificial intelligence. In particular, the invention relates to medical device software adjunct to endoscopy systems that assists the physician in fast and accurate identification and classification of polyps and other abnormalities.

2. Background of Related Art

Endoscopy procedures are performed by gastroenterologists in detection, diagnosis and treatment of various abnormalities including pre-cancerous polyps, ulcers, and inflammation of the digestive tract. Gastroenterologists and assisting technicians observe live video of digestive tract screening produced by an endoscope camera on a large video monitor.

A colonoscopy (lower endoscopy) screening procedure is one of the most effective screening and intervention procedures for colorectal cancer. It is used by gastroenterologists in detection, diagnosis and removal of various abnormalities including pre-cancerous polyps, ulcers, and inflammation of the colon. Colon abnormalities like polyps are organic in nature, they do not have a fixed shape or size or texture unlike man-made objects typically used in Common Objects in Context (COCO) data used to train conventional object detection methods. With respect to use of object detection in an endoscopy application there are several characteristics of the polyps that make deep learning on them especially challenging, unlike deep learning of object detection methods using conventional COCO data.

Given the characteristics of different polyps, detection, and classification of the polyps for annotation purposes for purposes of training deep learning algorithms is a very time-consuming exercise even for expert physicians. Full identification cannot be easily determined by looking at a single polyp-containing-image in isolation. Occasionally, the expert must be assisted by the video clip to accurately determine the region of polyp for annotation in a polyp-containing-image.

From the camera perspective, there could be several polyp look-alikes (and not actual polyps—also known as false positives) inside the colon, especially more so when the polyp is far from the viewing camera. Conventional deep learning approaches would highlight such false positive objects, causing severe distraction and inaccurate influence to the physician.

For instance, some of the challenges are: (1) That the same polyp might look different from different camera perspectives, different depths of field, and/or under varying illumination. (2) Because the light source in an endoscopy probe is often quite near to the polyp, the polyp in near view might look very bright and saturated with one color. (3) Once the endoscope is in the colon, the background context information surrounding the polyp looks almost similar throughout, regardless of the location of the endoscope inside the colon. (4) Polyps do not often have a well distinguished boundary from their surroundings and thus tend to merge into the background color, often making it difficult even for a trained human eye to detect them.

Given the above challenges, conventional pre-trained object detection models built on a COCO dataset cannot be readily used to detect polyps in video images.

SUMMARY OF THE INVENTION

A method of enhancing training of a colon polyp detector using a deep learning-based object detection algorithm in accordance with some embodiments of the invention comprises gathering a polyp early appearance image training dataset that includes a plurality of video clips each including an initial unfocused image of a polyp that is just starting to appear in frame. The plurality of video clips in the initial portion including the initial unfocused image of the polyp are sampled at a first sampling rate to generate polyp early appearance image training data. A remainder portion of the plurality of video clips is sampled at a second sampling rate, the second sampling rate being slower than the first sampling rate, to generate polyp image training data. The colon polyp detector is trained with both the polyp early appearance image training data and with the polyp image training data.

A method of enhancing training of a colon polyp detector using a deep learning-based object detection algorithm in accordance with another embodiment comprises detecting a polyp equipment insertion appearance image in each of a plurality of procedure videos. A portion of each of the plurality of procedure videos that immediately precedes the polyp equipment insertion appearance image is extracted to generate equipment insertion-determined polyp training clips. The colon polyp detector is trained with the equipment insertion-determined polyp training clips.

A method of indicating presence of a colon polyp using a deep learning-based colon polyp object detection algorithm in accordance with yet another embodiment comprises fetching a current frame as an inference image frame of a procedure video running in real-time. A colon polyp is inferred within the current frame of the procedure video using a deep learning-based colon polyp object detector. An output of the inference is overlaid onto a latest-fetched video frame of the procedure video running in real-time and not on the inference image frame.

A method to improve accuracy of inference of a polyp during deep learning based colon polyp object detection in accordance with yet another embodiment comprises inferring in parallel using a plurality of object detectors wherein each of the plurality of object detectors specializes in inference on a differently transformed colored space of an input image. Detected polyps are tracked by assigning a unique ID to each polyp detected across image frames to improve suppression of intermittent false positives. A reinforcing deep learning classifier post deep learning object detection algorithm is applied to further confirm polyp presence to thereby decrease false positives.

One object of the invention is to improve detection performance by expanding training dataset for a deep learning algorithm using domain specific (colon image) data adaptation, augmentation, and data mining.

Another object of the invention is to efficiently extract colon polyp images for labeling and training that may only span a few seconds from colon procedure video recordings that can last 10 minutes or more.

Another object of the invention is to autonomously detect colon polyp images during live procedures or procedure recordings that are missed by conventional colon polyp object detection algorithms struggle to detect and hence identification as good candidates for new training data for the object detection algorithm for colon polyps.

Another object of the invention is to reduce false positives and false negatives associated with colon polyp detection using deep learning-based object detection algorithms.

Another object of the invention is to improve early detection of colon polyps by reducing the time interval between when the polyp first appears in a video to when it is detected and highlighted by deep learning-based object detection algorithms.

Another object of the invention is to train an object detection algorithm on different image transformation datasets that complement each other at the inference time to improve the accuracy of the overall polyp detection in the colon.

Another object of the invention is to decouple the video frame fetching process from frame inference process during colon polyp object detection processing.

Another object of the invention is to post-process overlay the inference result on top of the latest fetched frame during colon polyp object detection processing.

BRIEF DESCRIPTION OF THE DRAWINGS

The patent or application file contains photographs in color. Copies of this patent or patent application publication with color photographs will be provided by the Office upon request and payment of the necessary fee.

Features and advantages of the present invention will become apparent to those skilled in the art from the following description with reference to the drawings, in which:

FIG. 10 shows an automated pre-process of generating new training data from polyp clip extraction in an abnormal case where a video clip of a configurable length prior to, and after detection of equipment presence for polyp removal, which was no preceded by an automatically detected polyp, and also a process of differentiating between tissue sample and polyp removal, in accordance with the principles of the present invention.

FIG. 14 shows a process of bounding box tracking to reduce intermittent false positives, in accordance with the principles of the present invention.

DETAILED DESCRIPTION OF ILLUSTRATIVE EMBODIMENTS

Polyps can occur in multiple varieties (pedunculated, flat, and sessile), and detection of flat varieties of polyps can be significantly more difficult than detection of pedunculated or sessile varieties of polyps. Flat polyps almost always visually merge into the background with truly little variation from the background context. Because of this, flat polyps tend to be missed more frequently by physicians using conventional methods.

Given that flat polyps have more chances of being missed by the physician, the present inventors have appreciated that it would be particularly important and of great value to be able to implement deep learning approaches to aid physicians in spotting polyps—particularly in spotting the flat varieties of polyps.

Object detection is a computer vision technique for finding objects of interest in an image. Object classification merely classifies an object of interest. Object detection both classifies and locates objects of interest in an image, and thus object detection is more complex than object classification.

Conventional object detection can be used to locate and classify existing objects in any one image and can be used to label detected objects with rectangular bounding boxes that indicate an amount of confidence of the existence of any detected object.

However, conventional object detection methods are not adequate to detect endoscopic abnormalities such as polyps in an endoscopic video reliably, accurately, and quickly, particularly in a live video stream.

Conventional object detection methods can be categorized into two main types: Region proposal-based object detection, and regression classification-based object detection.

A region proposal-based object detection method follows a traditional object detection pipeline to generate proposals for regions at first, and then to classify each generated proposal into a different object category. Exemplary region proposal-based object detection methods mainly include R-CNN, SPP-net, Fast R-CNN, Faster R-CNN, R-FCN, FPN and Mask R-CNN.

A regression classification-based object detection method regards object detection as a regression or classification problem, adopting a unified framework to achieve results (categories and locations) directly. Exemplary regression classification-based object detection methods mainly include MultiBox, AttentionNet, G-CNN, YOLO, SSD, YOLOv2, DSSD, DSOD and YOLOv3.

Figure 1:
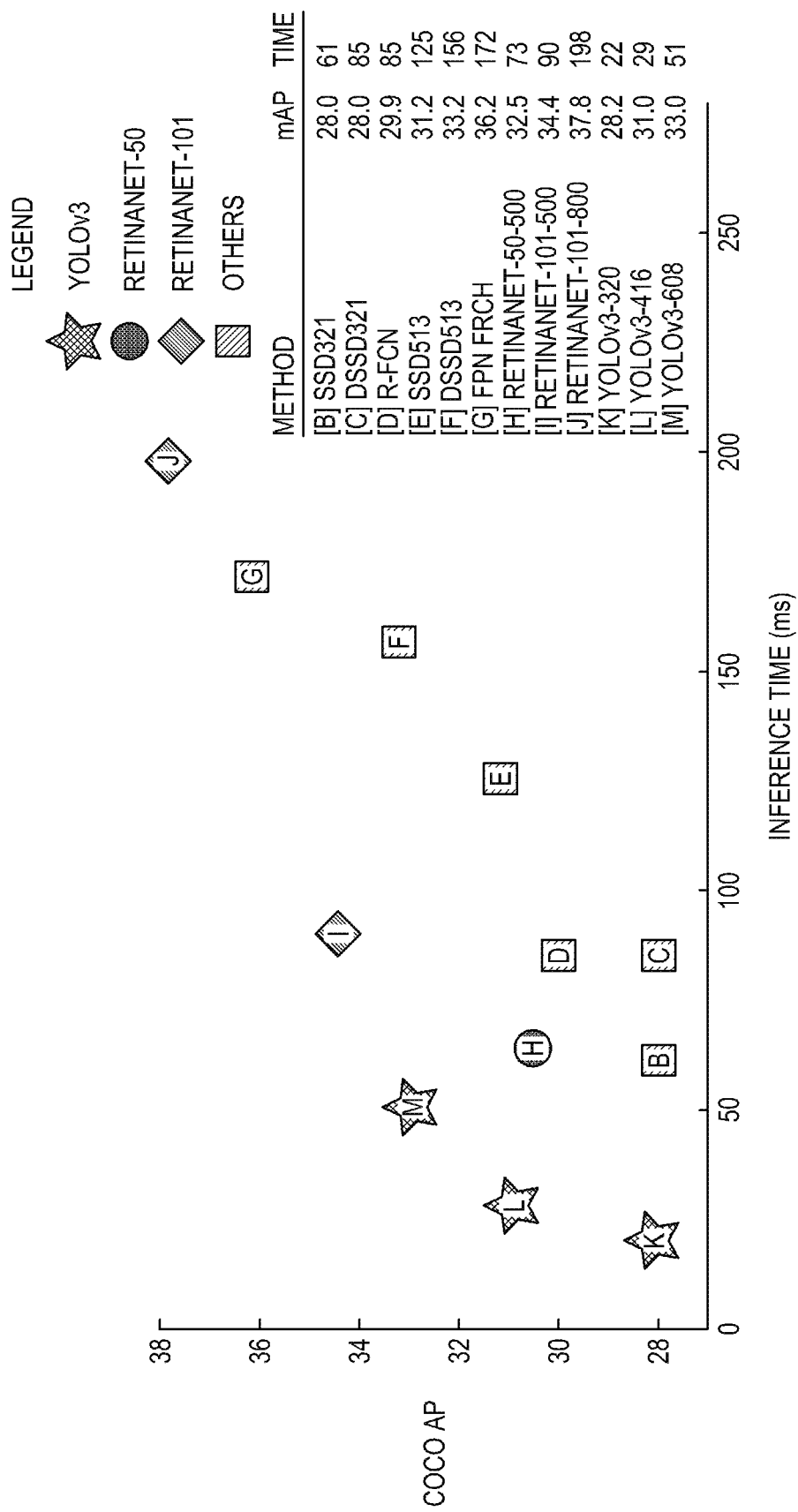
FIG. 1 shows a comparison of performance (mAP vs. inference time) of various conventional types of object detection methods.

FIG. 1 shows a comparison of performance (mAP vs. inference time) of various considered object detection methods. Shown in FIG. 1 is a comparison of various types of:
  SSD (Single Shot Detection)
  DSSD (Deconvolutional Single Shot Detector)
  R-FCN (Region-based Fully Convolutional Network)
  FPN (Feature Pyramid Network)
  RetinaNet (Retina Net)
  YOLO (You Only Look Once)
Not all possible object detection methods are shown in FIG. 1. The numbers suffixing these object detection model names indicate network/image parameters. For example, the present inventors have determined YOLOv3-832×480 as being suitable for use in disclosed embodiments. Here, "832×480" signifies the input resolution of images, i.e., 832×480 pixels and has been selected to preserve the aspect ratio of an input video stream which is 1920×1080 pixels.

The object detection methods depicted in FIG. 1 were trained upon a Common Objects in Context (COCO) dataset consisting of approximately 330,000 images with 1.5M object instances.

The inventors herein have appreciated that not all (and in fact very few) conventional object detection methods would be suitable for use in an endoscopy system. As is seen from the performance values shown in FIG. 1, regression classification methods and especially YOLO family of methods perform faster. The inventors have thus determined all other parameters considered equal, that the YOLO family of object detection methods, if appropriately trained, would be best suited for use in real-time object detection in endoscopic applications.

In particular, of the currently available object detection methods, the inventors herein have determined that the family of "You Only Look Once" methods (e.g., currently available YOLOv3), with training in accordance with the present invention, runs much faster (least amount of latency) in the given application than do other known object detection methods. Importantly, as explained herein, the inventors have appreciated that conventional training of a YOLOv3 object detector would not be suitable for use in an endoscopy system.

Given the above characteristics of a polyp, even if a deep learning algorithm for an object detector for an endoscopy system is trained upon a substantial amount of training data covering a variety of polyps, it may not provide an adequate enough performance to aid physicians in improving their ability to detect polyps.

Adaptation of Object Detection for Endoscopy

1.) Use of Transfer Learning to Maximize Training Data

Transfer learning is used to reduce the need for significant amounts of new data to adapt otherwise conventional object detection methods to a new domain such as in the detection of objects in colonoscopy images.

Sophisticated models such as deep neural networks typically require enormous resources, data, time, and computing power to create. However, with transfer learning they become far more accessible. The basic premise for transfer learning lies in the fact that the fundamental patterns for properly matched different classes may look similar, and hence they can be re-used without the need to retrain entirely from scratch.

The inventors have recognized that a model which has already been trained on a task for which labeled training data is plentiful would be better able to handle a new but similar task with far less data. Use of a pre-trained model often speeds up the process of training the model on a new task and can also result in a more accurate and effective model overall.

Figure 2:
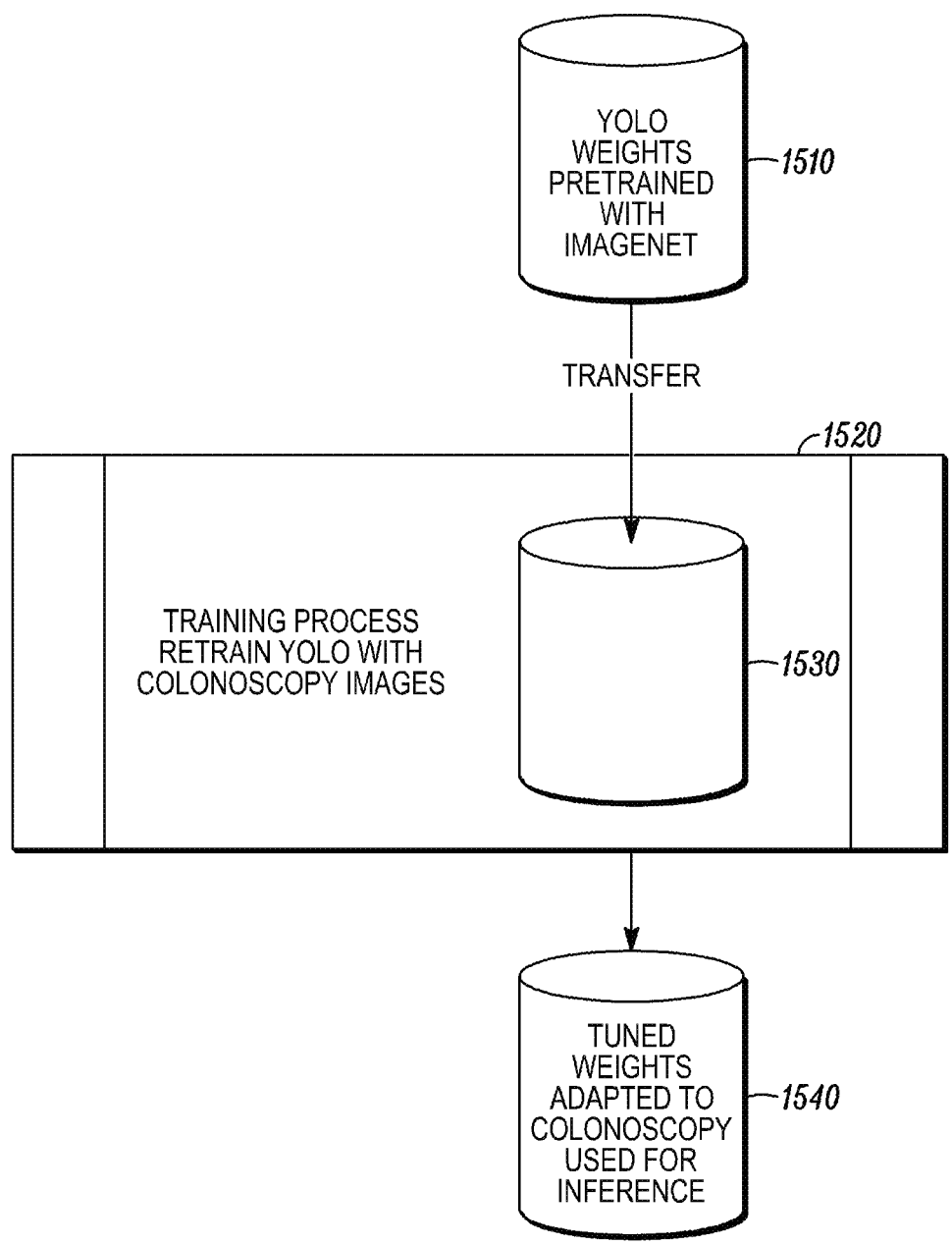
FIG. 2 shows incorporation of transfer learning in colon polyp detection algorithm training, in accordance with the principles of the present invention.

FIG. 2 shows incorporation of transfer learning in colon polyp detection algorithm training, in accordance with the principles of the present invention.

In particular, as shown in step 1510 of FIG. 2, a database is created with YOLO weights pretrained with imageNet data.

In step 1530, as part of the training process the YOLO object detection detector is retrained with colonoscopy images.

In step 1540, tuned weights are adapted to colonoscopy used for inference.

2.) Training Data Collection by Searching Video for Equipment Insertion

Figure 3:
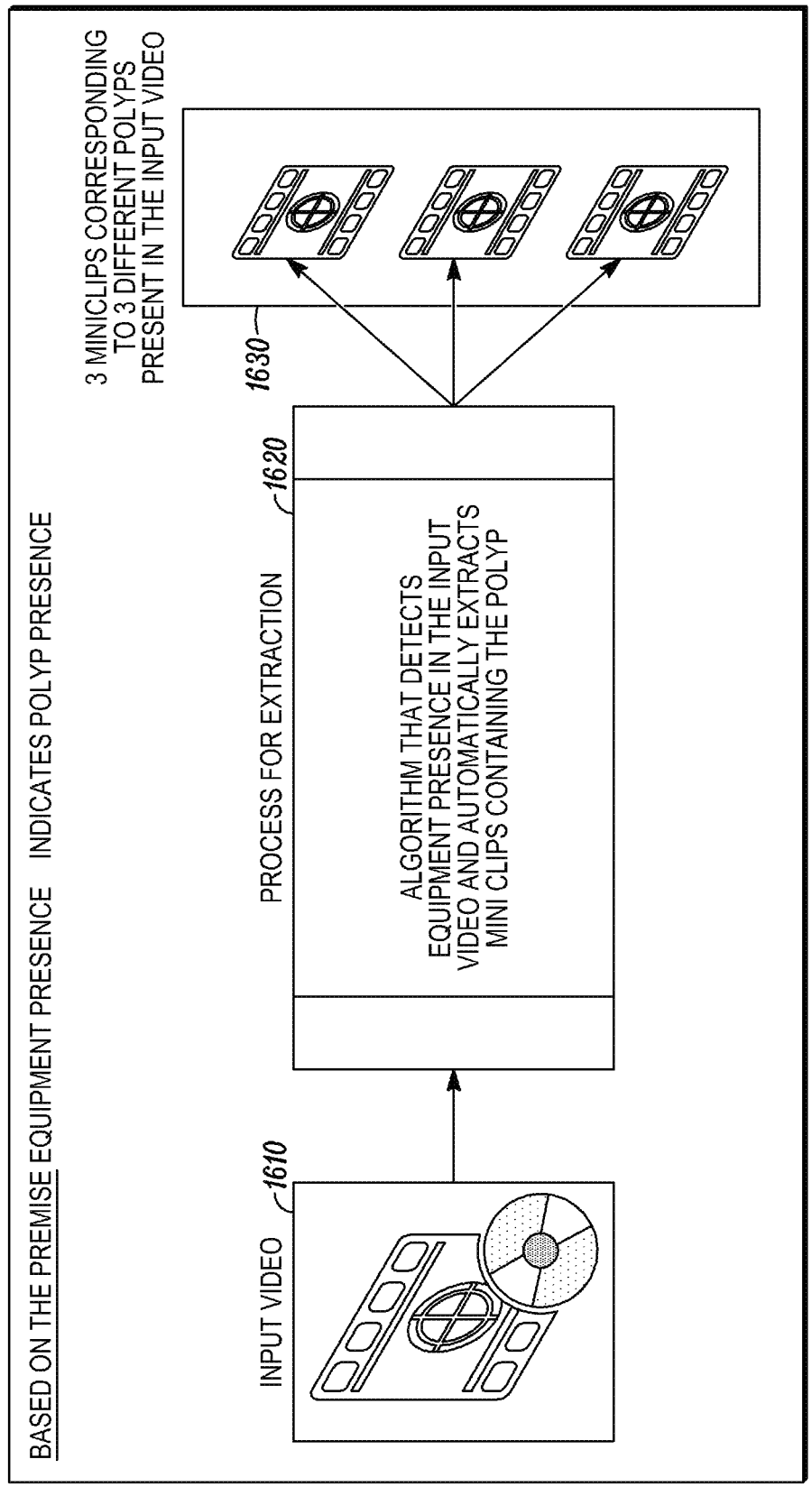
FIG. 3 shows training data obtained from polyp images efficiently extracted from video clips isolated to those clips which precede equipment insertion procedures, and polyp clip extraction for efficient training data identification and extraction, in accordance with the principles of the present invention.

FIG. 3 shows training data obtained from polyp images efficiently extracted from video clips isolated to those clips which precede equipment insertion procedures, and polyp clip extraction for efficient training data identification and extraction, in accordance with the principles of the present invention.

As shown in step 1610 of FIG. 3, video of endoscopy procedures is input into a method in accordance with the invention which crops the original length of endoscopy videos to much smaller clips of only relevant video.

In step 1620, automatic extraction of short, mini video clips containing a polyp is accomplished by detecting the presence of medical equipment inserted for use in extraction of a polyp or other colon feature.

In step 1630, a plurality of short, mini video clips each corresponding to a polyp identified by the physician are extracted.

Adaptation and optimization of generic object detection algorithms to a new domain (i.e., endoscopy) in accordance with the present invention requires new training methods specific to detection of relevant features in endoscopy. For adaptation and optimization of an otherwise conventional object detection algorithm to detection of colon polyps, specialized training of these object detection algorithms on colon polyp images is necessary.

Before a specialized database for use to train an object detection algorithm such as YOLO can be created, suitable training images of colon polyps must be collected, identified, and labeled. Unlike other domains, medical imaging including colon polyp images is not easy to come by, particularly when the present invention specifically seeks multiple views of the same polyp for superior performance.

The easiest method of collecting such a dataset is to acquire video recordings of entire colonoscopy procedures. Unfortunately, these videos may span 10 minutes or more on average in length and the actual portion where polyp images may be present may only be a few tens of seconds for each polyp. The inventors hereof have appreciated that training an object detection algorithm with such video recordings would result at best with low grade performance and at worst with an extremely inefficient colon polyp detector.

Figure 4C:
FIGS. 4A to 4C show images including different equipment types that are commonly used for polyp extraction and biopsies in view.
Figure 4B:
Figure 4A:
Figure 5D:
FIGS. 5A to 5D shows examples of valid spatial augmentation for colon images by flipping, zooming and rotating original image.
Figure 5C:
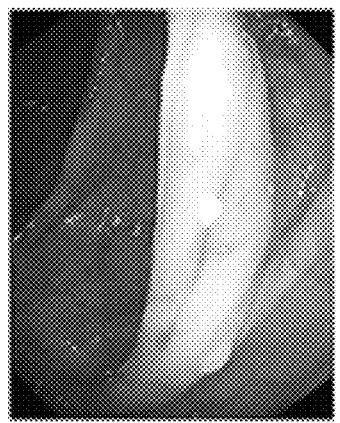
Figure 5B:
Figure 5A:
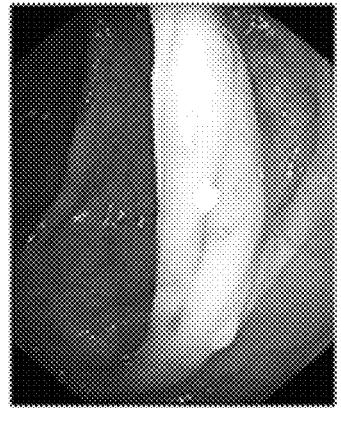

The inventors have appreciated that it is not efficient to manually review and search entire colonoscopy videos to identify and cull the videos down to smaller subsets of videos. The inventors have also appreciated that interestingly, since these recordings are of actual colonoscopy procedures, the presence of a polyp is typically followed by insertion of equipment (e.g., forceps, snare, etc.) to remove it. For instance, FIGS. 4A to 4C show images including different equipment types that are commonly used for polyp extraction and biopsies in view.

In accordance with the principles of the present invention, this aspect is exploited by pre-processing colonoscopy procedure videos to identify the presence of inserted equipment. This may be accomplished using appropriate object classification algorithm that has been trained to detect the presence of certain types of inserted equipment (e.g., forceps, snare, etc.) Classification task requires lesser amount of training data than object detection, so this approach results in overall polyp detector training efficiencies.

As shown in FIG. 3, the object detection algorithm pre-processes entire colonoscopy procedure video recordings and generates smaller video clips spanning a desired configurable time period before and after the inserted equipment is detected.

Preferably one video clip is generated for each polyp (and hence each equipment insertion), typically spans only a few tens of seconds. In this way manual searching of polyps in the full length of each colonoscopy procedure recording is not necessary, and the resulting shorter video clips of colon polyp images can not only be identified and extracted for training much more efficiently, but the trained polyp detector also becomes much more accurate and efficient.

3.) Augmenting Training Data by Shifting and/or Rotating Images at Random Angles Deep learning of object detection systems require significant amounts of data to avoid overfitting. Since colonoscopy data is different from regular natural images, it is possible to use novel data augmentation methods in colonoscopy data.

In certain embodiments of the present invention the existing training data is augmented by duplicating some or all existing training data and applying some transformations to the data. For instance, an image or video clip (and its annotation) is shifted horizontally to generate new training data. In colonoscopy, since the camera can rotate around its axis freely, the present invention rotates an image and its annotation by random angles to produce additional valid training data points, for example as depicted by example transformations shown in FIGS. 5A to 5D.

Figure 6C:
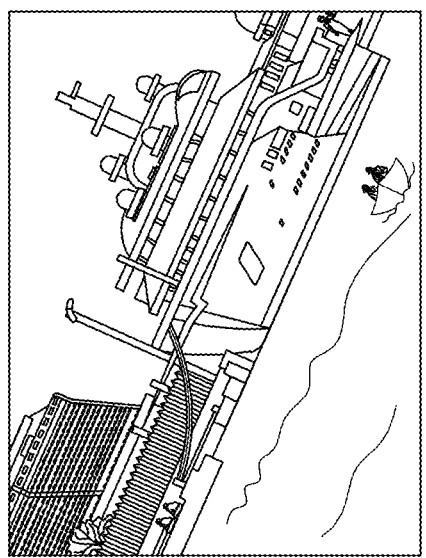
FIGS. 6A to 6C illustrate how the same spatial augmentation is not a valid training augmentation for real-world objects.
Figure 6B:
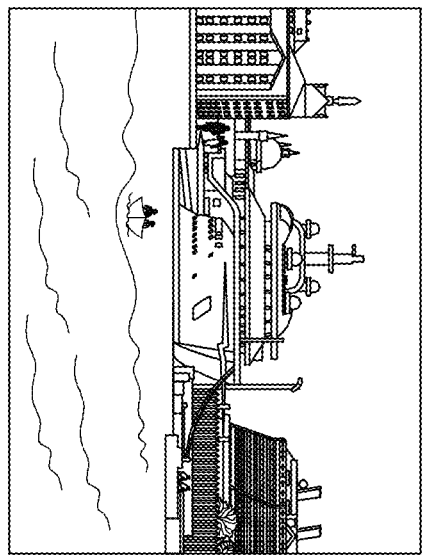
Figure 6A:
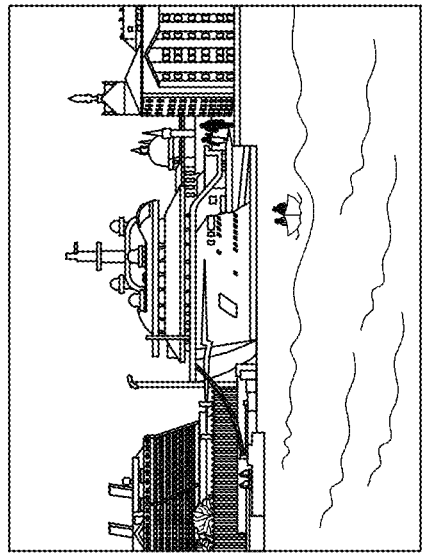
Figure 7D:
FIGS. 7A to 7D show examples of invalid color augmentation for Colon images, in accordance with the principles of the present invention.
Figure 7C:
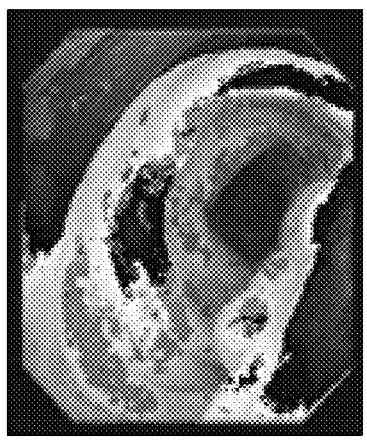
Figure 7B:
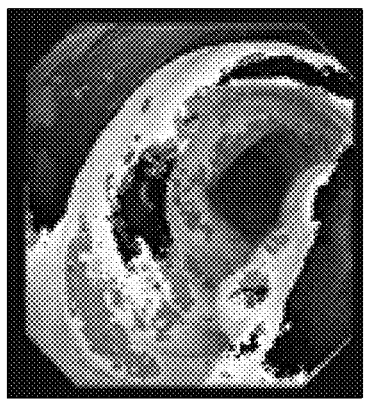
Figure 7A:
Figure 8D:
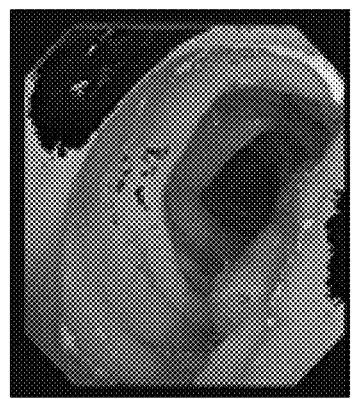
FIGS. 8A to 8D show examples of valid color augmentation for Colon images, in accordance with the principles of the present invention.
Figure 8C:
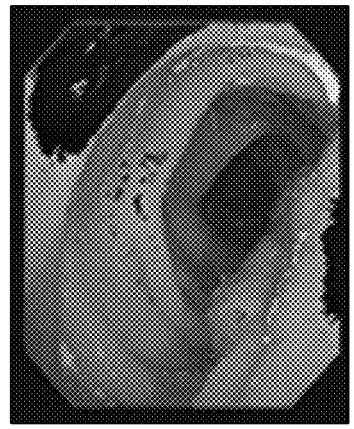
Figure 8B:
Figure 8A:

Note that this is not the case for natural images. For instance, FIGS. 6A to 6C illustrate how the same spatial augmentation (e.g., an exemplary rotated natural image) is not a valid training augmentation for real-world objects. Additionally, since colonoscopy image data is symmetric, augmented data may be created by applying transformations in accordance with other embodiments of the present invention including flipping the image or video clip horizontally and/or vertically.

4.) Training Data Augmentation Using Images Modified in Limited range of Hue, Saturation and/or Exposure While generating additional data by augmenting copied colon image data, the inventors have appreciated that it is important to be careful with, or completely avoid, transformations commonly used in other domains and with other datasets, especially those dealing with real world objects. Invalid training data can add a significant amount of inefficiency and noise to the dataset which would negatively impact the performance of the object detection algorithm.

For instance, data may be transformed using modification of hue, saturation, and/or exposure of existing images to generate new training data. However, unlike with object detection of natural images using datasets consisting of real-world objects, the variety in colon images is quite limited in terms of hue, saturation, and exposure. There is not a significant difference in color between colons of different people. The color range of any colon image is very narrow and mostly tinted towards shades of pink, red, and yellow, including for polyps as well as for the background. The colon images are lit by a point source of light (usually light with a yellow tint) which is located extremely close to the camera. Typically, most of the images have specular highlights that are clearly visible. Therefore, conventional data augmentation including modification of typical ranges for hue, saturation, and exposure will generate images that have unwanted colors that will not be seen in a colon, which is to be avoided to minimize noise in the training dataset.

For instance, FIGS. 7A to 7D depict sample images generated by general data augmentation by transformation in hue, saturation, and/or exposure. As can be observed, the images of FIGS. 7A to 7D do not look anywhere close to an actual colon image, and hence the inclusion of such images would only add noise to the training data, and decrease efficiency in the automated polyp detection.

In accordance with the principles of the present invention, polyp detection training data may be augmented using hue, saturation, and/or exposure using an empirically-determined small range for each of hue, saturation and exposure, to result in augmentation of the training data without adding noise.

Thus, to determine an appropriate range of hue, saturation and/or exposure that would be beneficial in training for polyp detection in accordance with the principles of the present invention, color histogram analysis on the entire training data set is preferably performed to determine the upper and lower bounds for the range of hue, saturation, and exposure actually seen, to guide color-based data augmentation for colon polyp training data. Subsequently, while performing color augmentation to a given image or video clip, the existing hue, saturation, and exposure values are measured and then compared against upper and lower limits for the entire dataset to determine the range of augmentation to apply. Such a process will ensure training data images with wide range of color hue, saturation, and exposure without producing unwanted images.

FIGS. 8A to 8D depict sample augmented images generated by transformation within the empirically determined range of hue, saturation, and exposure. As can be seen in FIGS. 8A to 8D, the hue, saturation and exposure are close to the hue, saturation, and exposure of typically seen colon images already existing in the training data.

5.) Emphasis in Training Data of Earliest Views of Detected Polyps

The inventors have appreciated that during scope withdrawal from the colon while the physician is investigating, there could be several blurred frames amid fewer clear frames in the video due to speedy movement of the scope. Even if a polyp were present during this phase, initially it may look small and distant from the camera. During this period there is a high chance that the physician will miss a significant object in the colon because the blurry image might not catch their eye.

Figure 9C:
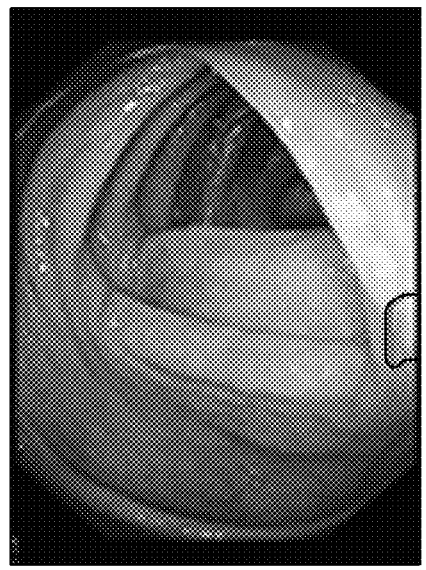
FIGS. 9A to 9C show examples of video frames of polyps just as they are starting to appear in view, in accordance with the principles of the present invention.
Figure 9B:
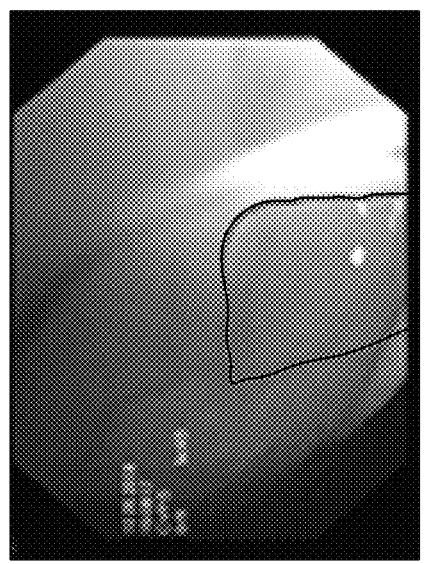
Figure 9A:
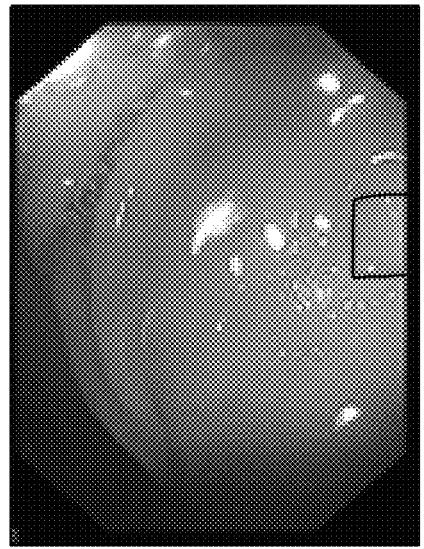

For instance, colon polyps as depicted via examples in FIGS. 9A, 9B and 9C are not easily recognizable because they are just beginning to appear in view of the camera. The inventors have appreciated that early detection of colon polyps by object detection methods is a key value-added feature for the physician as it can alert them of the presence of a polyp real-time, before the polyp is completely visible or identified by them, thereby increasing the length of time that the physician has to confirm the existence of a polyp, and overall reducing the chances that the polyp would be missed.

It is a normal practice to withdraw an endoscope at a certain speed while probing the colon for the presence of polyps. Typically, the physician will slow down the moment a polyp is suspected by the physician and as they get nearer. Thus, during the probe phase, speedy movement of the scope could result in several blurred frames prior to a clear view of a polyp, with the resulting slower movement of the scope yielding clearer frames with the polyp centered in the view.

If one were to take a video clip from the point of time when a polyp is just about to appear until the time when the polyp is clearly in view, then the duration for which the "polyp early appearance" occurs would be very short compared to the duration of the "polyp clearly in view". To extract training data from such a video clip in an evenly sampled fashion (e.g., say 1 in every 20 frames) would otherwise result in more "polyp clearly in view" frames than the "polyp early appearance" frames, creating a natural training data bias towards "polyp clearly in view". The inventors have appreciated that such biased training data does not help the deep learning algorithm to alert for polyps detected during a "polyp early appearance" phase as the object detector will not have learned from enough "polyp early appearance" images to balance out the training created by the "polyp clearly in view" frames.

In accordance with the principles of the present invention, the polyp detector is purposely trained for early detection by oversampling training frames from video clips in a varying fashion such that "polyp early appearance" video intervals are sampled at a higher rate as compared to "polyp clearly in view" video intervals, thereby generating an approximately equal distribution of both categories within the training data.

Preferably only very highly blurred frames from "polyp early appearance" frames are excluded from the training data, with most blurred and early frames being annotated (even if the polyp is only partially visible) so that this training data is augmented with early-detection views of polyps emerging into the physician's view.

In other embodiments of the invention, a new metric is determined which tracks the real-time difference between when a polyp first appears in view in a video clip and when the polyp is first detected by the object detector. Using this difference tracked, the object detector is trained to minimize the tracked differences.

6.) Augmenting Training Data with Images of Missed Polyp Detection

While initially, for an object detector trained to detect colon polyps, images of any polyp are good candidates for inclusion in training. However, this may not necessarily be the case once the algorithm has been adequately trained. Once trained, additional training on similar images of polyp types that the algorithm has been previously trained on and/or is already performing capably in detection, will not significantly improve the performance of the detection algorithm.

Preferably, training data is augmented with failed detection clips where the object detector struggled to detect presence of a polyp. Video clips or images where the trained colon polyp object detection algorithm struggled or did not detect a polyp, or did not detect a polyp before the physician identified the polyp, may be oversampled to generate new training data used to help improve algorithm performance with such images.

In video clips where no polyp detection is immediately followed by equipment insertion to remove a polyp, are gathered for retraining of the object detection algorithm. If the presence of removal equipment is not preceded by a detected polyp by the object detection algorithm, then this type video clip is identified for augmented training of the object detector. A clip with images of such a polyp would be hence especially useful in expanding the current training dataset. The present invention does just that by generating a clip of configured length prior to, and after equipment presence which was not preceded by a detected polyp.

There are some instances in procedures, where the equipment is inserted for just taking tissue samples for biopsy and not for polyp removal. The presence of biopsy equipment is usually much shorter than it is for polyp removal. Such scenarios may not be of interest and can be differentiated and ignored for the duration of the presence of that biopsy equipment.

FIG. 10 shows an automated process for refining an object detection algorithm for use in endoscopy, in accordance with the principles of the present invention.

In particular, FIG. 10 shows a pre-process of generating new training data from polyp clip extraction in an abnormal case where a video clip of a configurable length prior to, and after detection of equipment presence for polyp removal, which was not preceded by an automatically detected polyp, and also a process of differentiating between tissue sample and polyp removal, in accordance with the principles of the present invention.

In step 1710 of FIG. 10, the pre-process determines if the object detector detected the polyp in the polyp occurring sequence.

If so, the pre-process moves to step 1720 where it is determined if the equipment detector detected the presence of surgical equipment. If so, in step 1740 the pre-process extracts a short, mini video clip used for reporting purposes. If the step of 1710 did not detect the polyp, the pre-process would instead move to step 1730 where it is determined if the equipment detector detected the presence of surgical equipment in the video image. If so, in step 1750, the pre-process extracts the frames from this mini clip so that they can be used for retraining the polyp detection algorithm.

Figure 11:
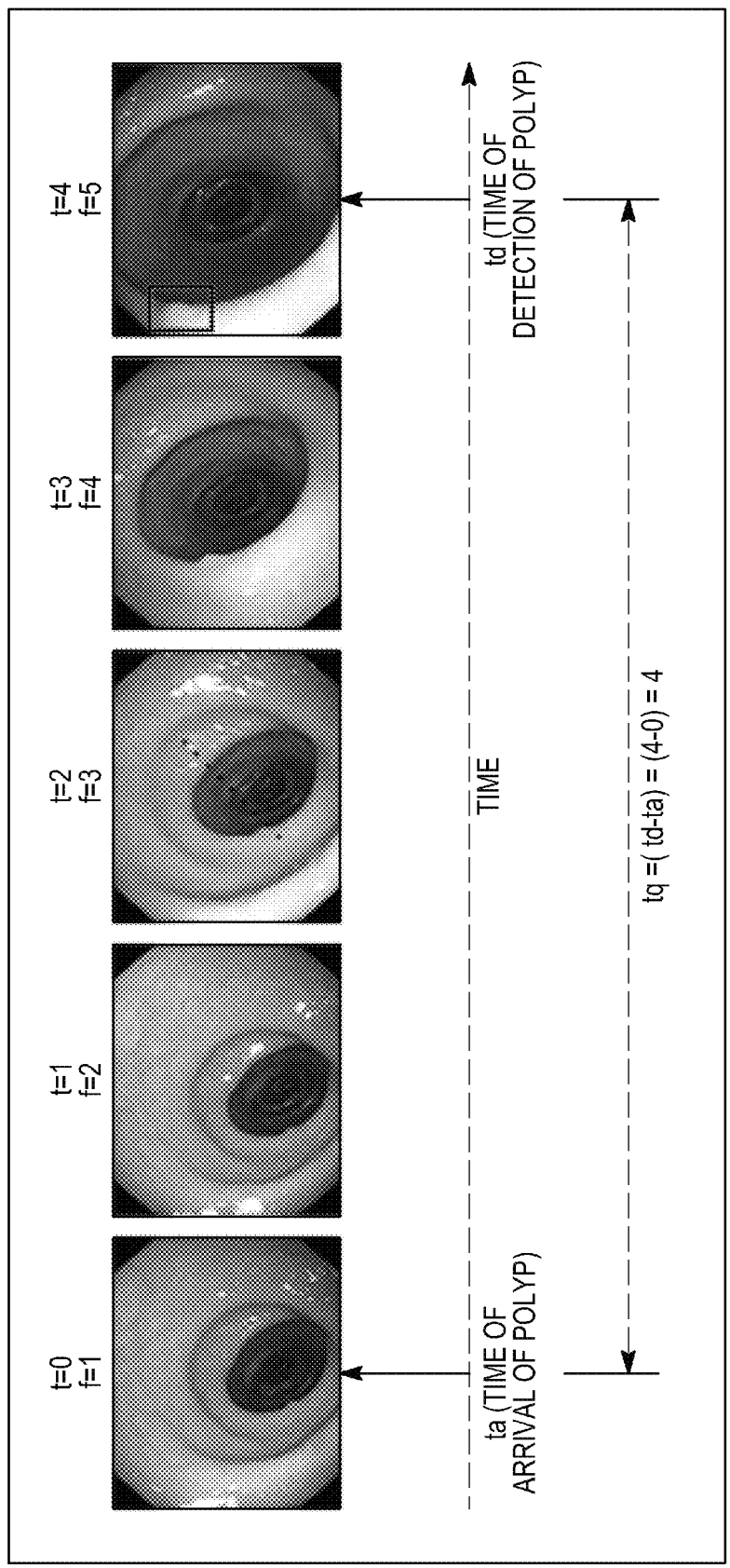
FIG. 11 illustrates selection of an object detection method based on how early it detects a polyp based on an early detection metric Tq, in accordance with the principles of the present invention.

7.) Object Detection Algorithm Version Selected Based on How Early a Polyp is Detected FIG. 11 illustrates selection of an object detection method based on how early it detects a polyp based on an early detection metric Tq, in accordance with the principles of the present invention.

In particular, for object detection algorithms, it is a common practice to select the model that yields best performance based on accuracy focused metrics (e.g., F1 score) at a given threshold. The operating threshold is then fine-tuned to meet the desired reduction in false positives/false negatives. However, the present inventors have appreciated that these conventionally used metrics minimize or ignore the time and speed factor with respect to an object appearing from out-of-frame. While it is desirable for object detection algorithms to accurately localize objects like the presence of a polyps, the present invention places a high importance in measurement of how "quickly" and how "early" a polyp is detected in a moving video by the system. This ensures that real-time feedback can be provided in a useable manner to the physician in an endoscopy procedure.

In accordance with some embodiments of the present invention, an additional new metric "time delay" Tq is created and compared between different object detection methods. Tq is defined as a measure of how long it takes the object detection algorithm to detect polyps. Tq=td−ta where to identifies the arrival frame of the polyp, and td is the frame in which the polyp is detected by a given object detection algorithm as illustrated in FIG. 11. In accordance with this embodiment, model weights and a threshold are selected based on the minimum time delay (Tq) in addition to achieving higher performance results on traditional metrics.

8.) Training a Reinforcing Deep Learning Classifier on Earlier-Detected Objects, for Use During Interference False positives, as depicted via examples in FIGS. 13A to 13C, can cause significant distractions to the physicians performing colonoscopy procedures—unnecessarily extending the length of the procedure, creating more eye fatigue, reducing trust in the product or feature, etc. Generally speaking, after a certain amount of training, significant improvements in false positives are not conventionally achievable without increasing false negatives.

Figure 12:
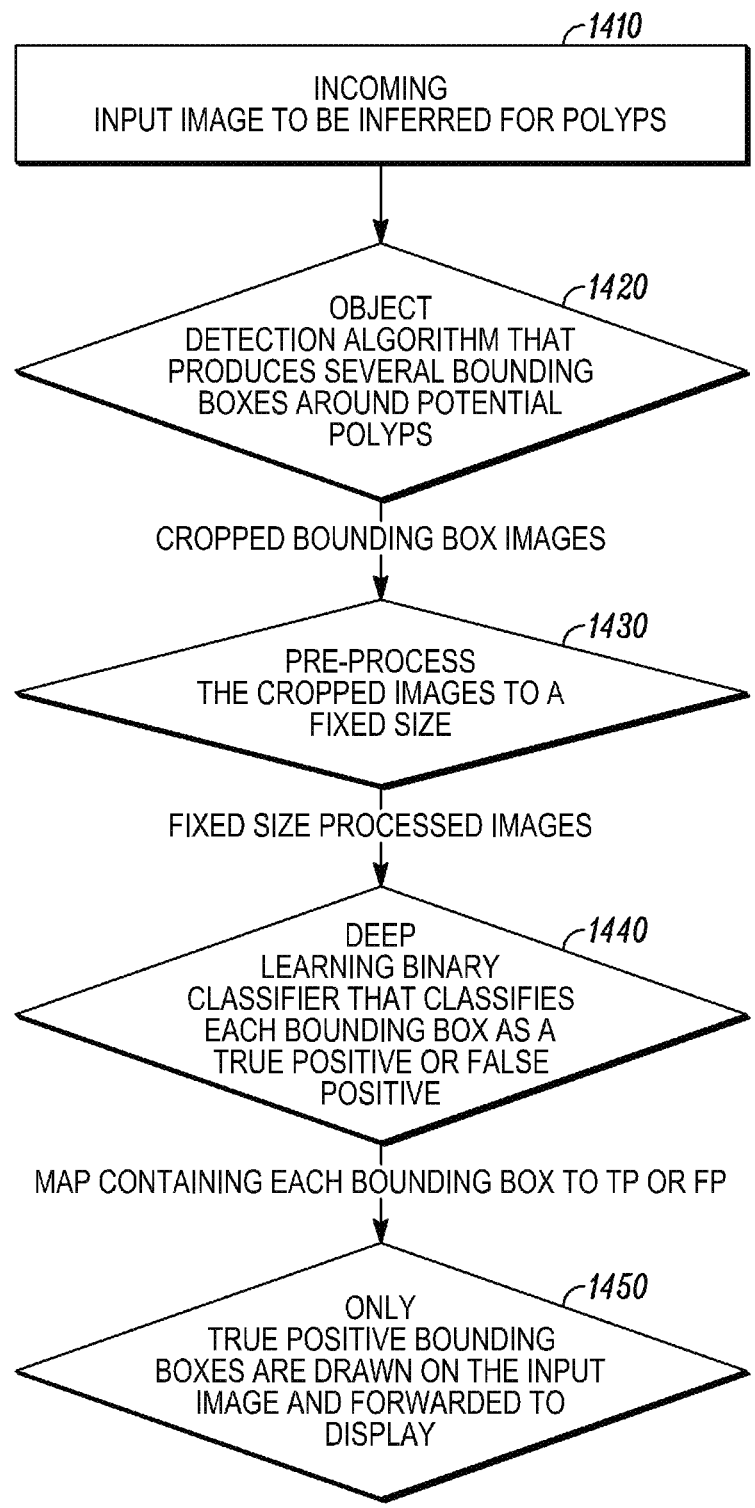
FIG. 12 shows a process of adding a reinforcement classifier in an object detection processing pipeline, in accordance with the principles of the present invention.

The approach in accordance with the invention as highlighted in FIG. 12 uses a reinforcing deep learning classifier method in step 1440 that is performed post-object detection to further refine the results and improve accuracy by reducing false positives. Training data for this reinforcing classifier is obtained from annotated recordings of live procedures or procedure recordings cropped to video portions including a polyp visible within a bounding box.

In preferred embodiments these training data are brought to a fixed size in step 1430 by padding the image background with black image data as necessary, importantly preserving their original aspect ratios. This is necessary because the deep learning classifier of step 1440 requires input of a fixed size image. Each of these training data images are labelled as 'True Positives' or 'False Positives'.

A binary deep learning classifier is trained on the above set of image data. In preferred embodiments this classifier is added on top of the original object detection model during inference. Any prediction done by the object detection model is input to this deep learning classifier for further reinforcement to check if the bounding box contents are classified as a 'True Positive' or a 'False Positive'. The dual reinforcement provided by classification of a Bounding Box as a 'True Positive' ensures reduction of false positives in the polyp detection process.

FIG. 12 shows a process of adding a reinforcement classifier in an object detection processing pipeline, in accordance with the principles of the present invention.

In particular, as shown in FIG. 12, a process of adding a reinforcement classifier to the processing of video for the presence of polyps includes an initial step 1410 of inputting an image to be inferred for polyps.

In step 1420, the processing of the image includes a step of processing for object detection to produce one or more bounding boxes around detected polyps (potential polyps) for confirmation by the physician.

In step 1430 the bounding box images are cropped to a fixed size.

In step 1440, a deep learning binary classifier classifies each bounding box as a "True Positive" or "False Positive".

In step 1450, only True Positive bounding boxes are drawn on the input image and forwarded to the display.

Figure 13A:
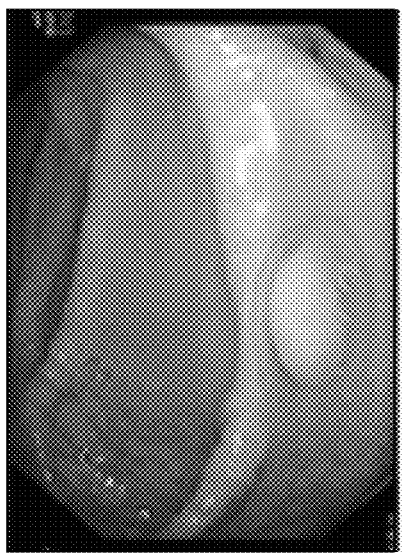
FIGS. 13A to 13C show examples of false positives for colon polyps due to 'lookalikes' of polyps which get incorrectly detected as polyps, thereby becoming false positives.
Figure 13B:
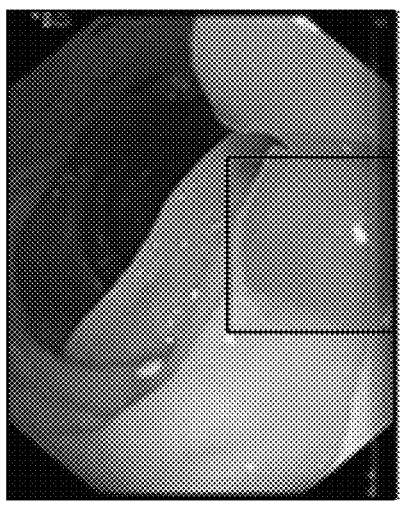
Figure 13C:
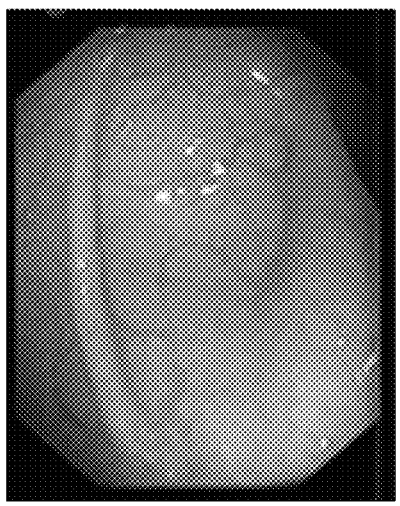

FIGS. 13A to 13C show examples of false positives for colon polyps due to 'lookalikes' of polyps which get incorrectly detected as polyps, thereby becoming false positives.

9.) Bounding Box Tracking to Reduce Intermittent False Positives

FIG. 14 shows a process of bounding box tracking to reduce intermittent false positives, in accordance with the principles of the present invention.

When an algorithm detects a polyp in a frame and the polyp is present in the picture, then it is called a 'True Positive'. When the algorithm does not detect a polyp in the frame though it is present in the picture then it is called a 'False Negative'. False negatives tend to cause a flickering effect on the bounding box in a polyp appearing frame sequence as it detects True Positives on several frames but intermittently missing on some intermediate frames. This bounding box flickering can be quite distracting and unpleasing to the eye of the physician. The inventors have appreciated that it would be helpful to persist the knowledge and information of past several frames to make a prediction on a current frame so that False Negatives are reduced, but this ordinarily might be thought to impact the inference time and latency as it would require higher computer resources to preserve the history of frames.

FIG. 14 illustrates an innovative approach to reduce intermittent False Positives using bounding box tracking.

The inventors have found that intermittent False Positives generally have the following characteristic features—they occur for very short duration (they are temporarily visible typically for 2 to 3 frames); and the algorithm confidence score for such False Positives is comparatively less than the confidence score for True Positives. Increasing the lower confidence threshold to reduce False Positives works to an extent, but it also reduces the True Positives.

In disclosed embodiments a positive prediction is tracked (True Positive/False Positive) on a certain frame across frames, using its bounding box center coordinates by assigning it a unique ID.

As shown in FIG. 14, a sequence of image frames 1810 to 1812 are presented for processing. Each image frame 1810 to 1812 is inferred on for and produce bounding boxes around potential polyps in the frame 1810 to 1812.

In step 1830 the process keeps track of the bounding boxes across past "n" frames and assigns a unique ID to each bounding box.

In step 1840, it is determined if the life span of the bounding box is lesser than the configured threshold. If so, then in step 1850 the bounding box is not displayed.

In other embodiments, the bounding box is purposely not drawn on the video frame on which it is determined, but rather on a later video frame. Preferably, the video frame on which the bounding box is drawn is a frame subsequent to a configured "frame delay" parameter, with a weighted confidence score across the "frame delay" number of frames is above the configured lower threshold value.

Improved Endoscopic Abnormality Detection

Figure 15:
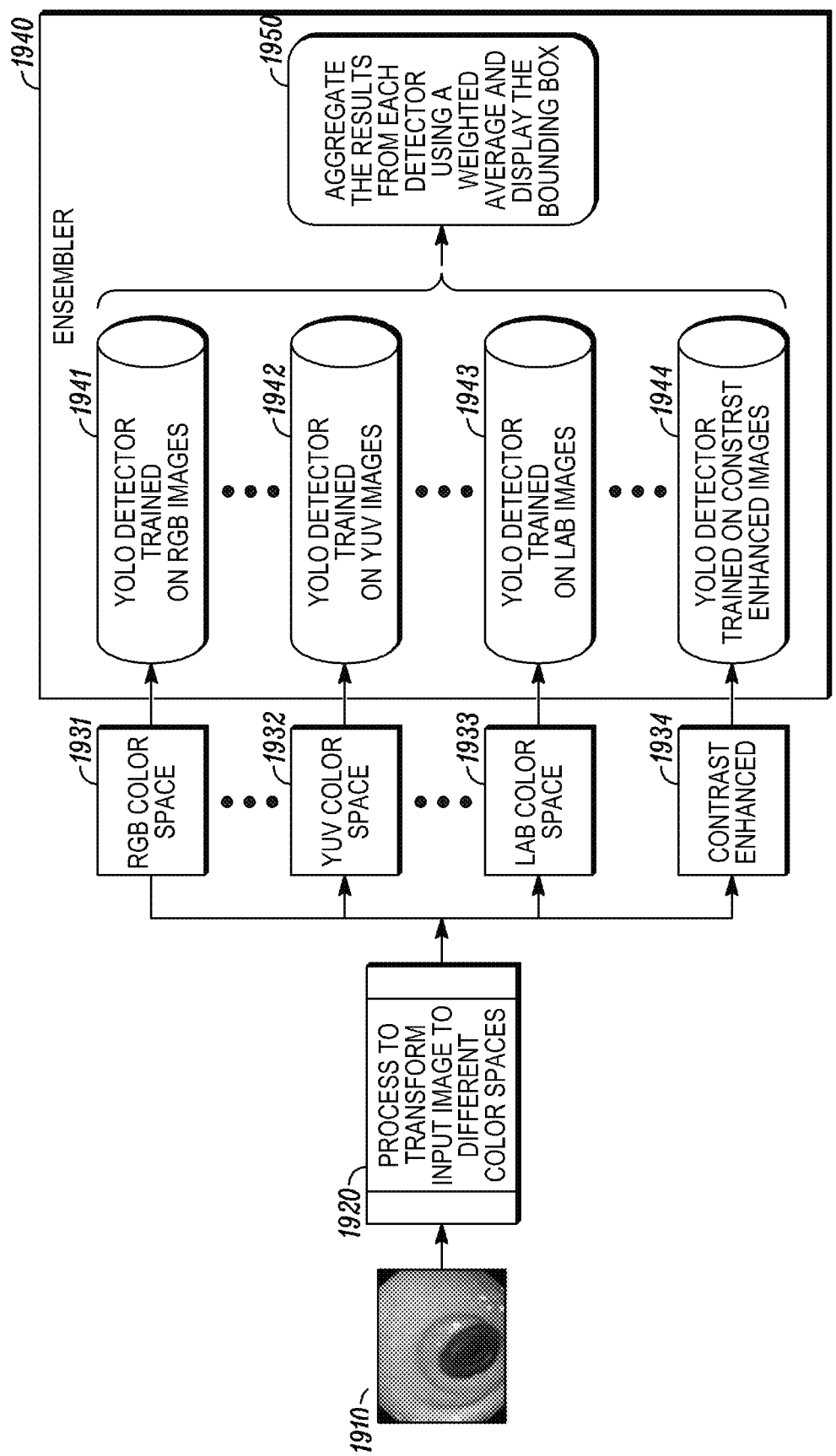
FIG. 15 shows a process of inferring using multiple detection models trained on different transformed datasets, in accordance with the principles of the present invention.

10.) Training Different Type Colon Polyp Detectors and Combining Them in Parallel During Inference FIG. 15 shows a process of inferring using multiple detection models trained on different transformed datasets, in accordance with the principles of the present invention.

Ensemble learning is a machine learning method that trains multiple models independently to solve the same task and runs them all at the test time and aggregates the results. This is well studied in the context of conventional image classification in general—but not at all to meet the challenges of fast and accurate polyp detection in the colon, especially when operating on diverse and complementary transformed datasets.

Typically, the images that are fed into the deep learning frameworks are RGB color space images for feature extraction. The convolutions operate on RGB channels and filter the features from these respective channels. However, there are hidden features in other transformed color spaces that are significant to learn. Assembling of different models that operate on each of these color spaces as exemplified in FIG. 15 together helps to increase the accuracy of polyp detection more than any single model would operating on a single-color space.

The present invention inputs several different transformations of the input image to different models, which produce diversified results that the inventors appreciated can complement each other in the use for training in a polyp detection application.

Figure 16B:
FIGS. 16A and 16B show a first example of transformation of a standard image in white light, to provide enhanced visualization of a colon mucosal surface and of abnormalities, in accordance with the principles of the present invention.
Figure 16A:

For instance, image transformations such as those depicted in FIGS. 16A and 16B are achieved through techniques like wavelength suppression, contrast, tone and surface enhancement, or operating in different color spaces besides RGB (e.g., LAB or YUV) to enhance visualization of the superficial micro vessel and mucosal surface structures by enhancing the subtle contrast of the irregularities of the colon mucosa.

In a minimum contrast environment as is found in the colon, some embodiments may implement a transformation such as certain wavelengths of light are suppressed so that other colors become exaggerated, creating increased contrast. In this case, items such as blood vessels, other tissue on the surface, etc. may visually stand out better in the altered-wavelength environment.

As shown in FIG. 15, an image 1910 is presented to a process 1920 to transform the input image 1910 to a plurality of different color spaces.

Exemplary color transformations of the input image 1910 include an RGB color space 1931, a YUV color space 1932, a LAB color space 1933, and a contrast-enhanced color space 1934.

An ensemble unit 1940 performs a polyp detection on each of the color transformations. Thus, an output of the RGB color space 1931 transformation of the input image 1910 is input to a YOLO polyp detector trained on RGB images 1941. An output of the YUV color space 1932 transformer is input to a YOLO polyp detector trained on YUV images 1942. An output of the LAB color space 1933 transformer is input to a YOLO polyp detector trained on LAB images 1943, and an output of the contrast-enhanced 1934 transformer is input to a YOLO polyp detector trained on contrast-enhanced images 1944.

Polyp detection output from each of the multiple detectors, e.g., from each of the YOLO detector trained on RGB images 1941, the YOLO detector trained on YUV images 1942, the YOLO detector trained on LAB images 1943, and the YOLO detector trained on contrast-enhanced images 1944, are aggregated by an aggregator 1950. The aggregator 1950 aggregates the results from each detector 1941-1944 using a weighted average, and if all agree on the presence of a polyp adds a bounding box in the appropriate region of the image 1910.

Some embodiments of the present invention provide a method of ensemble learning to improve accuracy of the model in detection of polyps. In accordance with the invention, multiple detectors using different transformations of the input image are used in parallel and applied simultaneously at the time of polyp inference. Results from each of the multiple detector models are aggregated to produce an aggregated result which considers the uncertainty of each of the models if used independently. If more models agree with a polyp detection, then that polyp detection will have a higher accuracy (i.e., 'True Positive') as compared to unaugmented models which may result in 'False Positives'.

If necessary or desired, the model may be made to be more conservative and accept only polyp detections in which all the multiple detectors agree on.

11.) Reduced Inference Time by Applying Inference Decision to Latest Frame Only

Figure 17:
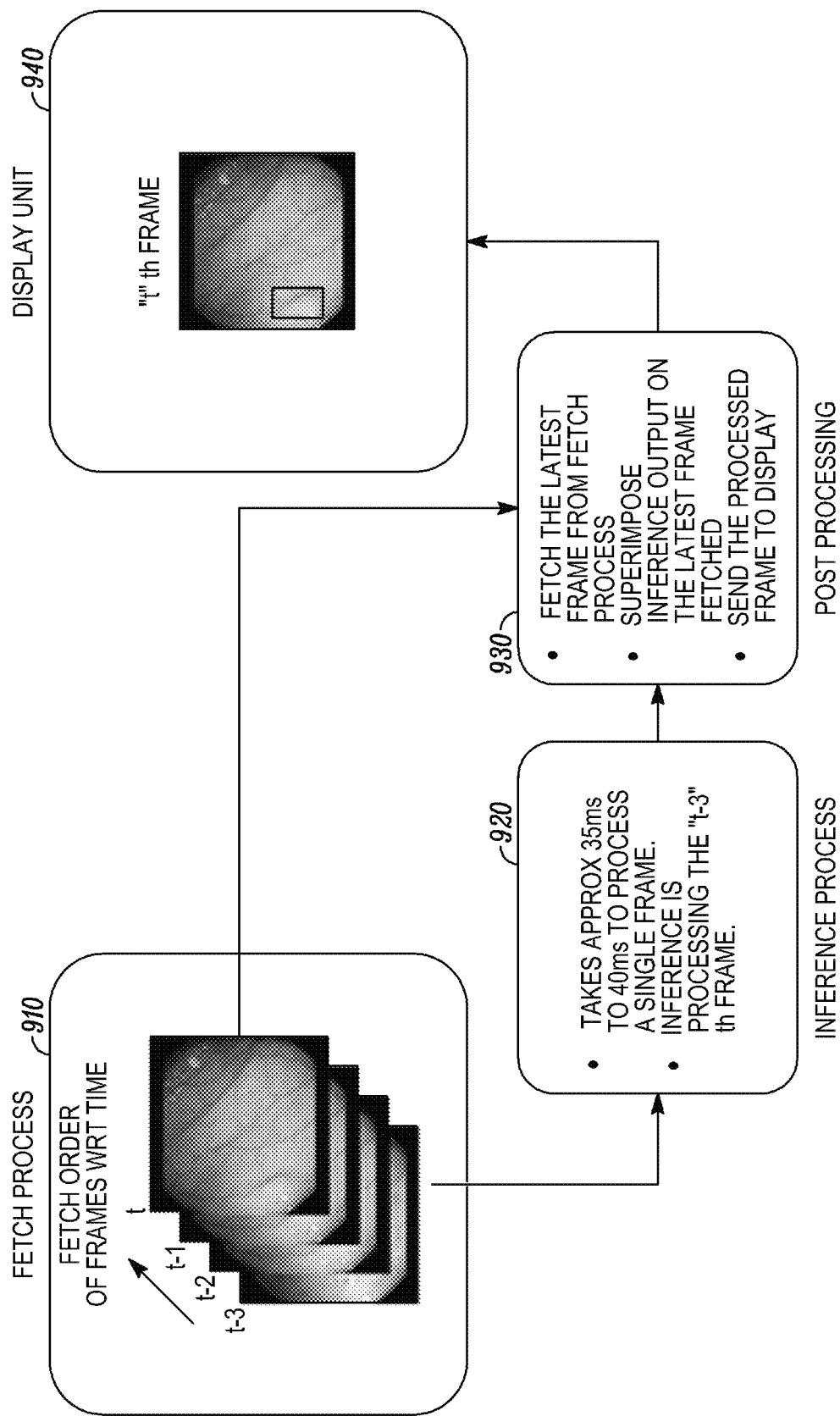
FIG. 17 shows inference performed on a previous image frame being applied to a latest fetched image frame, in accordance with the principles of the present invention.

FIG. 17 shows inference performed on a previous image frame being applied to a latest fetched image frame, in accordance with the principles of the present invention.

In particular, as shown in FIG. 17, a polyp detection system includes a fetch process 910, an inference process 920, post-processing 930, and output to a display monitor unit 940.

In the life cycle of an image frame t-3, t-2, t-1 and the latest frame t illustrated in the fetch process 910 of FIG. 17, from the time it is captured by the camera to the point it ends up on the display monitor 940, latency is introduced at several stages viz., during a camera capture process, by the video adapter used for streaming the frame to the computer, by the inference time of the "deep learning" software, and even during display of the processed frame.

The inventors consider that a response time of 50 ms to 100 ms is typically considered instantaneous for a human eye, which is significantly less than the measured end to end latency of AI-assisted video occurring in real-time.

When the physician moves or tilts a scope inside the colon, it is a human expectation to see an instantaneous response of the new view to where the scope has moved. This is a habituated correlation between the hand movement to the visual display that the mind is tuned to observe with the least amount of latency between the hand movement and the image frame appearing on the display monitor unit 940. Given that physicians typically perform eight to ten hours of such procedures during a day, any amount of extra latency (more than what is termed instantaneous) could cause severe distraction and could even lead to dizziness. Hence, the inventors have appreciated that it is highly desirable to reduce or eliminate any extra latency above 100 ms as it would lead to undesirable effects.

Thus, one of the major challenges of deep learning approaches is the inference time (i.e., the amount of time taken by the object detection method to determine if a polyp is present in the frame). Given the deep layered, complex architectures of neural nets, the processing demands even at the inference time is typically remarkably high. Added to this, there is another complexity that colonoscopy video frames are typically at a resolution of 1920×1080 arriving at an incoming rate of 30 FPS (frames per sec) or higher. Scanning each 1920×1080 incoming frame in real-time, using deep neural nets, for the presence of polyps and then highlighting them in real-time on the display monitor unit 940 without significant or even any latency is technically challenging.

A conventional deep learning object detection network such as YOLO requires at least 30+ milliseconds (ms) (e.g., on an RTX2080TI general processing unit) to process and infer on just an 832×480 image for polyp detection. The output of an inference process in accordance with the invention results in a set of bounding box coordinates indicating the likelihood of polyps' presence within a given image frame. But this step alone directly adds that amount of latency to the inference process, thus adding to the overall end to end latency.

FIG. 17 depicts the life cycle of a frame t that starts with fetching process 910 and goes through the inference process 920 and post processing 930 and is output to the display monitor unit 940. Typically, the incoming frame t is processed sequentially, i.e., the frame t that gets fetched goes through the inference process 920 and post-processing 930 and then the processed image is sent to the display monitor unit 940. For accuracy reasons, this sequential process is sometimes desirable when the camera moves quite fast relative to the scene and hence each incoming frame t contains substantially different information from the previous frame t-1. Also, such sequential process ensures a high level of bounding box positional accuracy on the objects detected in the frame t. But such sequential processing suffers from a high latency as the display of each sequentially processed frame t-1 must wait for each step 910-940 to get completed before it can proceed to next frame t.

In the context of real-time colonoscopy procedures, typically the physician moves the camera in incremental steps (and does so slowly) to explore the colon in sufficient detail for the presence of polyps. Therefore, camera movement in an endoscopic procedure typically is not very rapid. Because of this, the inventors have appreciated that successive frames t-3, t-2, t-1, t over a short time interval in an endoscopic application are typically almost identical. Secondly, the drawing of a bounding box around a detected polyp is to alert the physician about the possible presence of a polyp in each frame. The inventors have appreciated that in an endoscopic application, even if the position accuracy of the bounding box is slightly off by few pixels, it does not significantly affect the notification to the physician and hence does not significantly impact the purpose of the bounding box.

For these stated reasons, the inventors herein have determined that each video frame need not essentially go through all of these sequential steps, and that efficiencies of latency reduction are achieved by decoupling the fetching process 910, the inference process 920, post-processing 930, and output to the display monitor unit 940 from one another. By decoupling these processes there is flexibility to display whatever comes first (bounding box coordinates or fetched frame). We set off a timer trigger at the end of of every 20 ms (or so) and decide if a new fetched frame arrives first at the end of 20 ms, then the existing bounding boxes are drawn on the newly fetched frame and send to display. Conversely, if bounding box co-ordinates are computed first at the end of 20 ms and a new fetched frame has not arrived yet, then we can display the newly computed bounding box coordinates on the existing fetched frame. This process also ensures selective inference on frames and does not necessarily need to infer on all the fetched frames.

A real-time endoscopic application for an object detector would necessarily require real-time deep learning methods, and real-time deep learning methods would require real-time inference. One thought might otherwise be to generate inference on each frame in isolation without preserving any information of the past frames, owing to the unaffordable computer demands of such methods. However, in accordance with embodiments of the present invention, latencies are minimized or eliminated by outputting the results of the inference process 920 and post-processing 930 performed on a given frame (e.g., frame t-3) is overlaid not over that frame t-3 on which the processing was inferred but instead onto a latest fetched frame t.

Thus, for instance during the 30+ ms inference time on a given image frame t-3, a few more additional frames t-2, t-1, t will have been fetched by the fetching process 910 (fetching happens at an approximate speed of 60 frames per second i.e., fetching one frame in every 16 ms). So at least 2 to 3 new frames t-2, t-1, t will have been fetched during the 30+ ms inference time of the given image frame t-3. In accordance with a post-process method of the present invention, only the latest frame t from the fetching process 910 is superimposed with the latest inference result (bounding boxes) rather than the frame t-3 on which the inference was processed. The inventors have observed that this technique reduces the end to end latency of a YOLO process by almost 35 to 40 ms when fetching is operated at 60 FPS.

This invention can be applied to both live procedures (if the object detection algorithm is deployed and in use by physicians) as well as procedure recordings (by using the object detection algorithm to process the procedure files as opposed to live video captures).

The present invention is premised on improved quality and efficiency of training data by increasing the attention paid in preparation of the object detection training data. A deep learning object detector produces results only as good as the quality of its input training data. Ensuring a good variety and coverage of training data enables the deep learning algorithm to yield better results with little variance during inference time.

While the invention has been described with reference to the exemplary embodiments thereof, those skilled in the art will be able to make various modifications to the described embodiments of the invention without departing from the true spirit and scope of the invention.

What is claimed is:

1. A method of enhancing training of a colon polyp detector using a deep learning-based object detector, comprising:

gathering a polyp early appearance image training dataset that includes a plurality of video clips each including an initial image of a polyp that is just starting to appear in frame;

sampling the plurality of video clips in the initial portion including the initial image of the polyp at a first sampling rate to generate polyp early appearance image training data;

sampling a remainder portion of the plurality of video clips at a second sampling rate, the second sampling rate being slower than the first sampling rate, to generate polyp image training data; and training the colon polyp detector with both the polyp early appearance image training data and with the polyp image training data.

2. The method of enhancing training of a colon polyp detector using a deep learning-based object detector according to claim 1, further comprising:

sampling the remainder portion of each of the plurality of video clips after the initial region at a lower image sampling rate than for the initial region.

3. The method of enhancing training of a colon polyp detector using a deep learning-based object detector according to claim 1, wherein the initial portion has a predetermined fixed length of time.

4. The method of enhancing training of a colon polyp detector using a deep learning-based object detector according to claim 1, wherein:

the colon polyp detector training is further enhanced by additionally training the colon polyp detector with a complementary transformed image dataset including a transformation of the polyp early appearance image training data, in addition to training with the polyp early appearance image training data and the polyp image training data;

whereby accuracy of polyp detection is increased at time of inference by the addition of transformed images in the training.

5. The method of enhancing training of a colon polyp detector using a deep learning-based object detector according to claim 4, wherein:

the transformation of the polyp early appearance image training data is at least one of shifting and rotating an image within the polyp early appearance image training data.

6. The method of enhancing training of a colon polyp detector using a deep learning-based object detector according to claim 4, wherein:

the transformation of the polyp early appearance image training data is generated by shifting an image within the polyp image training data.

7. The method of enhancing training of a colon polyp detector using a deep learning-based object detector according to claim 4, wherein:

the transformation of the polyp early appearance image training data is generated by rotating an image within the polyp image training data.

8. The method of enhancing training of a colon polyp detector using a deep learning-based object detector according to claim 7, wherein:

the transformation rotates the image at a random angle.

9. The method of enhancing training of a colon polyp detector using a deep learning-based object detector according to claim 4, wherein:

the transformation of the polyp early appearance image training data is generated by altering at least one of hue, saturation, and exposure within a limited range.

10. The method of enhancing training of a colon polyp detector using a deep learning-based object detector according to claim 1, further comprising:

training the colon polyp detector to minimize a difference in time in the plurality of video clips between when the polyp first appears in frame, and when the colon polyp detector first detects that polyp.

11. The method of enhancing training of a colon polyp detector using a deep learning-based object detector according to claim 1, further comprising:

further training the colon polyp detector with images of missed polyp detection.

\* \* \* \* \*